(12) United States Patent
Sheetz et al.

(10) Patent No.: US 6,982,150 B2
(45) Date of Patent: Jan. 3, 2006

(54) SYSTEM AND METHOD FOR IDENTIFYING PROTEINS INVOLVED IN FORCE-INITIATED SIGNAL TRANSDUCTION

(76) Inventors: Michael P. Sheetz, 560 Riverside Dr., Apt. 7b, New York, NY (US) 10027; Yasuhiro Sawada, 54 Morningside Dr., Greenwich, CT (US) 06830

( * ) Notice: Subject to any disclaimer, the term of this patent is extended or adjusted under 35 U.S.C. 154(b) by 0 days.

(21) Appl. No.: 10/914,924

(22) Filed: Aug. 10, 2004

(65) Prior Publication Data

US 2005/0084843 A1    Apr. 21, 2005

Related U.S. Application Data

(63) Continuation of application No. PCT/US02/15794, filed on May 16, 2002.

(60) Provisional application No. 60/355,927, filed on Feb. 11, 2002.

(51) Int. Cl.
*G01N 33/53* (2006.01)

(52) U.S. Cl. ............... 435/7.2; 435/7.21; 435/7.23; 435/287.1; 435/288.3

(58) Field of Classification Search ............... 435/7.2, 435/7.21, 7.23, 7.32, 287.1, 288.3
See application file for complete search history.

(56) References Cited

U.S. PATENT DOCUMENTS

| | | | |
|---|---|---|---|
| 4,839,280 A | 6/1989 | Banes | 435/285 |
| 4,940,853 A | 7/1990 | Vandenburgh | 435/240.23 |
| 5,348,879 A | 9/1994 | Shapiro et al. | 435/240.241 |
| 5,486,457 A | 1/1996 | Butler et al. | 435/7.2 |

OTHER PUBLICATIONS

Sawada et al., 2002, "Force transduction by Triton cytoskeletons" J Cell Biol., 156(4):609-615.
Balaban et al., 2001, "Force and focal adhesion assembly: a close relationship studied using elastic micro-patterned substrates," Nat. Cell. Biol. 3: 466-472.
Grill et al., 2000, "Polarity controls forces governing asymmetric spindle positioning in the *Caenorhabditis elegans* embryo," Nature 409, 630-633.
Riveline et al., 2001, "Focal Contacts as Mechansosensors: Externally Applied Local Mechanical Force Induces Growth of Focal Contacts by an mDial-dependent and ROCK-independent Mechanism" J. Cell Biol. 153:1175-1185.
Sawada et al., 2001, "Rap1 is involved in cell stretching modulation of p38 but not ERK or JNK MAP kinase," J. Cell Sci. 114:1221-1227.
Walev et al., 2001, "Delivery of proteins into living cells by reversible membrane permeabilization with streptolysin-O," Proc Natl Acad Sci U S A. Mar. 13;98(6):3185-3190.

(Continued)

*Primary Examiner*—David Redding

(57) ABSTRACT

The present invention relates to a cytoskeletal system composed of purified components which allow for the identification of key proteins involved in mechanotransduction. The system comprises a cytoskeleton network deficient in force-dependent proteins, exogenous proteins in contact with the cytoskeleton network, a means for applying a force to the cytoskeleton network, and a means for identifying any of the exogenous proteins that bind to the cytoskeleton network when a force is applied to the cytoskeleton network, wherein proteins identified are involved in mechnotransduction. The invention further relates to a method for identifying proteins involved in mechanotransduction using the cytoskeletal system of the present invention. The identification of key players involved in mechanotransduction allows for the identification of agents capable of inhibiting or enhancing mechanotransduction.

53 Claims, 8 Drawing Sheets

OTHER PUBLICATIONS

Bang et al., 2000, "Association of Focal Adhesion Kinase with Fibronectin and Paxillin Is Required for Precartilage Condensation of Chick Mesenchymal Cells" Biochem Biophys Res Commun 278:522-529.

Damien E, Price JS & Lanyon LE., 2000, "Mechanical strain stimulates osteoblast proliferation through the estrogen receptor in males as well as females," Journal of Bone and Mineral Research, 15 2169-2177.

Grodzinsky et al. 2000 "Cartilage tissue remodeling in response to mechanical forces," Annu. Rev. Biomed. Eng. 2:691-713.

Kippenberger et al., 2000, "Signaling of Mechanical Stretch in Human Keratinocytes via MAP Kinases," J Invest Dermatol.; 114:408-412.

Yano et al., 2000, "Paxillin a and Crk-associated substrate exert opposing effects on cell migration and contact inhibition of growth through tyrosine phosphorylation" Proc. Natl. Acad Sci 97:9076-9081.

Galbraith and Sheetz 1999, "Keratocytes Pull with Similar Forces on their Dorsal and Ventral Surfaces" J Cell Biol 147:1313-1323.

Horwitz and Parsons, 1999, "Cell migration-Movin' on" Science 286(5442):1102-1103.

Okuda et al., 1999, "Shear Stress Stimulation of p130cas Tyrosine Phosphorylation Requires Calcium-dependent c-Src Activation," J Biol Chem, vol. 274(38): 26803-26809.

Yamazaki et al., 1999, "The Molecular Mechanism of Cardiac Hypertrophy and Failure," Ann NY Acad Sci.; 874: 38-48.

Glogauer et al., 1998, "The Role of Actin-binding Protein 280 in Integrin-dependent Mechanoprotection," J Biol Chem., vol. 273, Issue 3, 1689-1698.

MacKenna et al., 1998, "Extracellular Signal-regulated Kinase and c-Jun NH2-terminal Kinase Activation by Mechanical Stretch Is Integrin-dependent and Matrix-specific in Rat Cardiac Fibroblasts," J. Clin. Invest. 101: 301-310.

Chen C.S. et al., 1997, "Geometric Control of Cell Life and Death" Science 276:1425-1428.

Choquet et al., 1997, "Extracellular matrix rigidity causes strengthening of integrin-cytoskeleton linkages," Cell. 88, 39-48.

Harte et al., 1996 "p130Cas, a Substrate Associated with v-Src and v-Crk, Localizes to Focal Adhesions and Binds to Focal Adhesion Kinase" J. Biol Chem 271:13649-13655.

Ishida et al., 1996, "MAP Kinase Activation by Flow in Endothelial Cells: Role of $\beta1$ Integrins and Tyrosine Kinases," Circ Res 79: 310-316.

King et al., 1997, "Phosphatidylinositol 3-Kinase is Required for Integrin-Stimulated AKT and Raf-1/Mitogen-Activated Protein Kinase Pathway Activation" Mol. Cell Biol. 17:4406-4418.

Pommerenke et al., 1996, "Stimulation of integrin receptors using a magnetic drag force device induces an intracellular free calcium response," Eur. J. Cell Biol. 70:157-164.

Olejnik et al., 1995, "Photocleavable biotin derivatives: a versatile approach for isolation of biomolecules" Proc Natl. Acad. Sci USA 92:7590-7594.

Timmenga EJ et al., 1991, "The effect of mechanical stress on healing skin wounds: an experimental study in rabbits using tissue expansion," Br J Plast Surg. 44(7):514-9.

Burridge et al., 1990, "Actin-membrane interaction in focal adhesions," Cell Differ Dev 32, 337-42.

Komuro et al., 1990, "Stretching cardiac myocytes stimulates protooncogene expression," J. Biol. Chem., 265: 3595-3598.

Wirz et al., 1990, "Calcium mobilization and exocytosis after one mechanical stretch of lung epithelial cells," Science 250: 1266-1269.

Ryan TJ, 1989, "Biochemical consequences of mechanical forces generated by distention and distortion," J Am Acad Dermatol Jul.:21(1):115-30.

Dennerll TJ et al., "Tension and compression in the cytoskeleton of PC-12 neurites. II: Quantitative measurements," J Cell Biol. Aug.;107(2):665-74.

Akiyama et al., 1987, "Geinstein, a Specific Inhibitor of Tyrosine-specific Protein Kinases" J Biol. Chem 262:5595-5595.

Chen et al., 1987, "Peroxiosmal beta-oxidation enzyme proteins in adrenoleukodystrophy: distinction between X-linked adrenoleukodystrophy and neonatal adrenoleukodystrophy," Proc Natl Acad Sci USA. Mar., 84(5): 1425-1428.

Sawada and Sheetz, Nov. 16, 2001. Meeting abstract: American Society for Cell Biology, Cytoskeleton stretch causes focal contact protein binding. Program #:2469, Board # B265.

A
Before stretch    Stretched

B

Before stretch   Stretched   Relaxed from stretch

US 6,982,150 B2

SYSTEM AND METHOD FOR IDENTIFYING PROTEINS INVOLVED IN FORCE-INITIATED SIGNAL TRANSDUCTION

The present application is a continuation of International Patent Application No. PCT/US02/15794 filed May 16, 2002, which published as International Publication No. WO 03/06933 A1 on Aug. 21, 2003, in English, claiming priority under 35 U.S.C. § 119(c) to U.S. Provisional Patent Application Ser. No. 60/355,927 which was filed Feb. 11, 2002, each of which is hereby incorporated by reference in its entirety.

This invention was made with government support under NIH Grant No. GM 23345. Therefore, the government has certain rights in the invention.

BACKGROUND OF INVENTION

The present invention relates to a cytoskeletal system, and to the use of a cytoskeletal system, composed of purified components for the identification of key proteins involved in mechanotransduction.

The present invention is based on the observation that mechanical stress induces a redistribution of cytoplasmic focal contact proteins to cytoskeletal structures.

Mechanotransduction, or force-initiated signal transduction, is the process by which cells convert mechanical stimuli into a chemical response. Mechanical forces, through the initiation of signal transduction, play a critical role in cellular development (Grill et al. 2001 Nature 409:630–633), wound healing (Timmenga et al. 1991 Br. J. Plast. Surg. 44:514–519), cell growth (Damien et al. 2000 J. Bone Miner. Res. 15:2169–2177; Chen et al. 1997 Science 276:1425–1428), tissue remodeling (Grodzinsky et al. 2000 "Cartilage tissue remodeling in response to mechanical forces," Annu. Rev. Biomed. Eng. 2:691–713), and sensory functions, such as touch and hearing. As such, understanding the mechanism of and identifying the key proteins in mechanotransduction may be useful for, inter alia, the treatment of wounds (e.g. treatment of burns, injuries and post-surgical lesions), the treatment of cancer through the control of cell growth, the healing of bone fractures, and the treatment of sensory disorders, such as paralysis, hearing loss and poor vision.

Although it is not well understood, the cytoskeleton, the extracellular matrix (ECM), and various traditional signaling molecules play key roles in mechanotransduction. The cytoskeleton, composed of actin microfilaments, microtubules and intermediate filaments, serves as the structural backbone for the cell and provides a mechanism for cell motility. Mechanical force induces changes in cytoskeletal structures (Komuro et al. 1989, Ryan J. Am. Acad. Der. 21:115, Dennerll et al. 1988, J Cell Biol August;107(2): 665–74.), which may, in turn, be involved in the initiation of signal transduction.

Extracellular matrix (ECM) proteins, such as collagens, laminins, fibronectins, hyaluronans, and other proteoglycans, are secreted by cells and used by cells to mediate contact and adhesion to a solid substrate and also appear to be involved in cell-to-cell communication. The initiation of signal transduction by extracellular mechanical forces may be mediated through the interaction with various ECM proteins (MacKennan et al. 1998. J. Clin Invest. 101: 301–310).

In addition, various components of the mitogen activated protein (MAP) kinase cascades appear to be activated by mechanical forces (Kippenburger et al. 2000 J. Invest. Dermatol. 114:408–412; Yamazaki et al. 1999 Ann. NY. Acad. Sci. 874:38–48; Ishida et al. 1996 Cir. Res. 79:310–316; Sawada et al. 2001 J. Cell Sci. 114:1221–1227.) MAP kinases are important mediators of signal transduction from the cell surface via phosphorylation cascades. Several subgroups of MAP kinases have been defined, and each manifests different substrate specificities and responds to various distinct extracellular stimuli. Cell stretching (Kippenberger et al. 2000J. Invest. Dermatol. 114:408–412; Yarnazaki et al. 1999 Ann. NY Acad. Sci. 874:38–48) or shear stress from fluid flow (Ishida et al. 1996 Cir Res. 79:310–316), both of which are types of mechanical forces, have been shown to activate the following MAP kinase pathways: extracellular signal-regulated protein kinase (ERK); c-Jun amino-terminal kinase (JNK); and p38 kinase pathways. Upstream of MAP kinases, G proteins, such as Ras and Rap1, also appear to be involved in mediating a force-initiated signal. Rap1, for example, is activated by cell stretching and inactivated by cell contraction, whereas Ras is activated by cell contraction and inactivated by cell stretching (Sawada et al. 2001 J. Cell Sci. 114:1221–1227).

Mechanical stress may also be mediated by changes in ion channel activity (Wirtz and Dobbs, 1990 Science 250: 1266–1269; Pommerenke et al. 1996 Eur. J. Cell Biol. 70:157–164; Glogauer et al. 1998 J. Biol. Chem 273: 1689–1698; Okuda et al. 1999 J. Biol. Chem. 274:26803–26809). However, these studies, which have shown that mechanical stress is mediated through changes in ion channel activity, do not address the role of cytoskeletal proteins which may be involved at the initial site of signal transduction at the plasma membrane.

Focal adhesion/contacts are sites found on the plasma membrane where intracellular cytoskeletal elements come into contact with ECM proteins. Proteins localized to the focal adhesions/contacts, include p125 focal adhesion kinase (FAK), paxillin, vinculin and integrins. Cells adhere tightly to the underlying substrate and the ECM proteins at focal adhesions. This adhesion is mediated by the integrin family of heterotrimeric cell surface receptors. In addition, actin filaments appear to be bundled by integrin receptors at the focal adhesions (as reviewed by Burridge et al. 1990, Cell Differ Dev Dec 2;32(3):337–42). Thus, it has been hypothesized that focal adhesions may also serve at the site of mechanotransduction. Various studies show that mechanotransduction may occur at focal adhesions through the induction of changes to integrin-cytoskeletal bonds (Choquet et al. 1997 Cell 88:39–48) and cause redistribution of proteins to focal adhesions (Balaban et al. 2001 Nat. Cell Biol. 3:466–472).

To date, no system or method is known for the quick and reliable identification of key proteins involved in mechanotransduction. Accordingly, a need exists in the art for a system or method for identifying key proteins, such as cytoplasmic proteins, involved in mechanotransduction. In one embodiment of the invention, the focal adhesion proteins, which may mediate initial transduction of mechanical stress and play a critical role in the signaling to downstream cytoplasmic molecules, are identified.

SUMMARY OF THE INVENTION

The aforementioned need in the art is substantially satisfied by the present invention which in one aspect is a system of partially purified cellular structures for the identification of proteins involved in force-initiated signal transduction, also known as mechanotransduction. The system comprises a cytoskeleton network deficient in force-dependent proteins, exogenous proteins in contact with the cytoskeleton network, a means for applying a force to the cytoskeleton network, and a means for identifying any of the exogenous proteins that bind to the cytoskeleton network when a force is applied to the cytoskeleton network. The partially purified cytoskeleton network functions to detect deformation in the substrate and mediates interactions with exogenous proteins provided to the cytoskeletal structures. The system allows for the identification of exogenous proteins bound to the cytoskeleton network with the force applied thereto as proteins involved in mechanotransduction. As used herein, a force may be any mechanical force that can be applied to a cell, including, but not limited to stretching and contraction.

The present invention is based on the observation that mechanical stress induces a redistribution of cytoplasmic focal contact proteins to cytoskeletal structures. In one embodiment of the invention, the focal adhesion proteins, which may mediate initial transduction of mechanical stress and play a critical role in the signaling to downstream cytoplasmic molecules, are identified.

In another aspect, the present invention is a method of identifying proteins involved in mechanotransduction. The method comprises providing a cytoskeleton network deficient in force-dependent proteins, contacting the cytoskeleton network with exogenous proteins, applying a force to the cytoskeleton network, and identifying the exogenous proteins that bind to the cytoskeleton network when the force is applied thereto, wherein the exogenous proteins that bind to the cytoskeleton network are identified as proteins involved in mechanotransduction.

In still another aspect, the present invention is a method of screening for agents that inhibit or enhance mechanotransduction, which comprises providing a cytoskeleton network deficient in force-dependent proteins, contacting the cytoskeleton network with an identified force-dependent protein in the absence of an agent, applying a force to the cytoskeleton network, measuring an extent of binding of the identified force-dependent protein to the cytoskeleton network having the force applied thereto in the absence of the agent, contacting the cytoskeleton network with the identified force-dependent protein in the presence of the agent, measuring an extent of binding of each of the identified force-dependent protein to the cytoskeleton network having the force applied thereto in the presence of the agent, determining from the measurements described whether the presence of the agent increases or decreases the extent to which the identified force-dependent protein binds to the cytoskeleton network having the force applied thereto. The method according to the present invention may be useful in the identification of therapeutic agents for the treatment of, inter alia, cancer, hypertension or osteoporosis.

DETAILED DESCRIPTION OF THE INVENTION

The present invention provides for a system comprising a partially purified cytoskeleton network that can be used to identify proteins involved in mechanotransduction.

Figure 1:
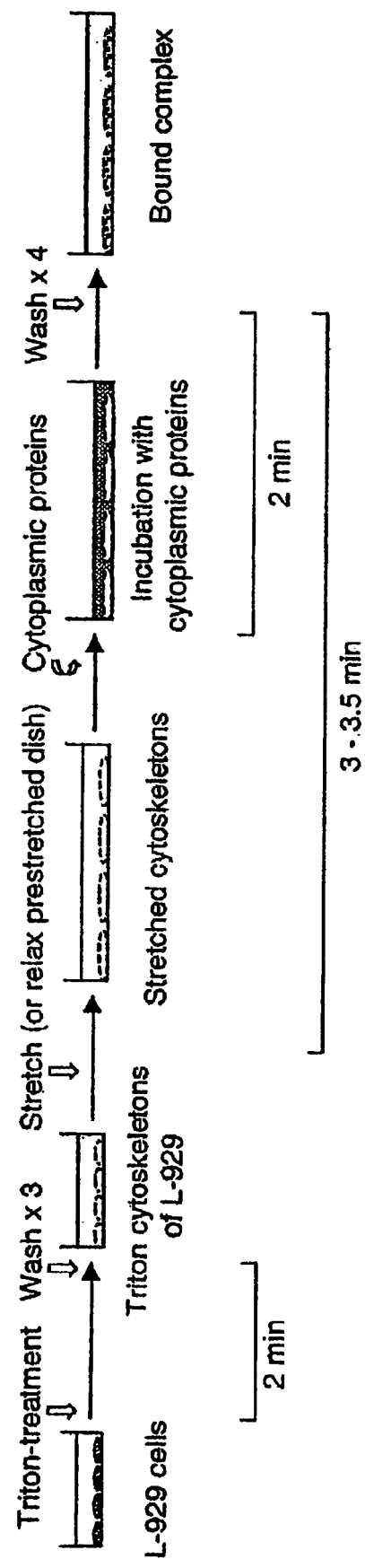
FIG. 1 shows the diagram for a protocol for stretch-dependent binding of cytoplasmic proteins.

The present invention is based on a cell-free system that mimics in vivo mechanotransduction events. The system comprises a partially purified cytoskeleton network deficient in force-dependent binding proteins and exogenous proteins, wherein the binding of the exogenous proteins indicates a role of the exogenous proteins in mechanotransduction. In a preferred embodiment of the invention, the cytoskeleton network is attached to a deformable elastomeric substrate so that the cytoskeleton network can detect deformation in the substrate. A force may be applied to the substrate to which the cytoskeleton network is attached. When exogenous proteins are added to the cytoskeleton network, key mechanotransduction proteins can be identified by their ability to bind to the cytoskeletal network upon application of force to the cytoskeleton network. As used herein, exogenous proteins may be any proteins that are not associated with the partially purified cytoskeleton network, including, but not limited to, a protein extract prepared from the same cells or different cells used to prepare the partially purified cytoskeleton network. An exemplary embodiment of the system is shown in FIG. 1 and further described below in the Examples section.

In one embodiment of the invention, the partially purified cytoskeleton network is obtained from cultured cells. For example, cells of interest may be gently disrupted so that force-dependent proteins are removed, at least in part, from the cellular structures and the cellular structures remain attached to a deformable elastomeric substrate. The remaining cellular structures are a partially purified cytoskeleton network attached to the substrate. A majority of focal contact, or focal adhesion, proteins, paxillin, focal adhesion kinase (FAK), p130Cas and vinculin are no longer associated with the cytoskeleton network. However, the disruption does not destroy integrin proteins, found at focal adhesions, which are crucial for the attachment of the cytoskeleton network to the ECM. The cytoskeleton network remains attached to the substrate even when a force is applied which causes deformation of the substrate, and which in turn applies a force to the cytoskeleton network, e.g., contraction or stretching.

In another embodiment of the invention, a component is used to obtain the partially purified cytoskeleton network deficient in force-dependent proteins. The component can be any component that may be added to cells to obtain a partially purified cytoskeleton network deficient in force-dependent proteins, such as a detergent, an alcohol, an enzyme, and the like. The component may be a component capable of permeabilizing cells. Alternatively, the partially purified cytoskeleton network deficient in force-dependent proteins may be obtained from conventional chromatographic techniques. For example, cells may be applied to a column which binds force-dependent proteins and removes them from the cytoskeleton.

In a preferred embodiment of the invention, detergents are used to permeabilize the cells. Most preferably, Triton X-100 is used to treat cells to obtain the attached cytoskeleton network deficient in force-dependent proteins. Other mild non-ionic detergents, such as Triton X-114, saponin, digitonin, CHAPS, CHAPSO, NP-40, and Brij-35, may also be used to treat the cells to obtain the cytoskeleton network. Alternatively, one may use various ionic, non-ionic, and anionic detergents to treat the cells to obtain the cytoskeleton network deficient in force-dependent proteins. One of skill in the art would be well aware of detergents applied at appropriate concentrations to obtain a detergent-insoluble cytoskeleton network which remains attached to the substrate. The stringency of the detergent treatment will affect the attachment of the remaining detergent-insoluble cytoskeletal structures.

Alternatively, the cellular membranes may be permeabilized and cytoplasmic contents released through various other treatments. These techniques may include the application of components, such as alcohols (e.g. methanol) and enzymes (e.g. streptolysin O (SLO)) (Walev et al. Proc Natl Acad Sci USA 2001 Mar. 13;98(6):3185–90).

Utilizing a substrate that is elastomeric mimics the in vivo conditions of mechanical forces on cells and tissues. In yet another embodiment of the invention, the cells are grown on a deformable elastomeric substrate. The deformation of the substrate may be initiated by physical contact with the substrate. In a further embodiment of the invention, the elastomeric substrate upon which the cells are are grown is attached to a stretch frame (Komura et al. 1990. J. Biol. Chem. 265:3595–3598). The stretch frame is designed so that it can be expanded by turning a horizontally mounted screw. Turning the screw causes the frame to expand, thereby uniaxially increasing the length of the elastomeric substrate and pulling out simultaneously by four corners.

A vacuum exerting a push or pull force on the substrate may also be used to initiate a deformation on the substrate. U.S. Pat. No. 4,839,280, which is incoparated herein by reference, discloses an apparatus and method of applying forces to an in vitro cell culture system. The apparatus incorporates the use of a tissue culture dish comprising wells each having an elastomeric bottom that may be stretched by evacuating the region beneath the bottom of the well. The upper surface of the well is designed for growing cells.

Alternatively, deformation may occur by applying a magnetic field as disclosed by U.S. Pat. No. 5,486,457, which is incorporated herein by reference. Twisting forces can be introduced to a cell using cell surface receptor specific attachment molecules conjugated to ferromagnetic microbeads that are manipulated by the controlled application of magnetic field.

In still another embodiment of the invention, the substrate upon which the cells are grown may be stretched so that the surface area is expanded. The surface area may be expanded from about 5% to about 50% of the original surface area of the substrate. Preferably, the surface area is expanded about 10% of the original surface area. In still another embodiment of the invention, the substrate upon which the cells are grown may be contracted so that the surface area is reduced. The surface area may be reduced from about 5% to about 35% of the original surface area of the substrate. Preferably, the surface area is reduced about 10% of the original surface area.

In a further embodiment of the invention, the substrate upon which the cells are grown is stretched prior to the plating of the cells. Alternatively, the substrate upon which the cells are grown is contracted prior to the plating of the cells.

In a still further embodiment of the invention, the substrate upon which the cells are grown is stretched after the cells have been plated on the substrate. Alternatively, the substrate upon which the cells are grown is contracted after the cells have been plated on the substrate.

In a preferred embodiment of the invention, the substrate upon which the cells are grown is stretched prior to the plating of the cells. At a later point, the substrate may be contracted or "relaxed" to obtain a smaller surface area and to contract the cells. The area may be reduced to the original "pre-stretched" area or contracted further to obtain an area smaller than the "pre-stretched" area.

The substrate upon which the cells are plated may be a tissue culture dish. The bottom of the well may comprise any material that is deformable, such as silicone, polystyrene, polypropylene, or any type of elastomeric material.

The invention provides for cells grown under in vitro tissue culture conditions. In a preferred embodiment of the invention, the cells are grown to subconfluent levels. When cells become confluent, the area of adherence to the matrix substrate may be decreased, causing a reduction in the adherence to the substrate.

The cells of the present invention may include cells of any type that are amenable to culture conditions. This may include primary cells, newly isolated from a host, or established cell lines. These cells include, but are not limited to, L-929 cells, HEK 293 cells, tumor cells, muscle cells, hair cells, neurons, cardiac smooth muscle cells, endothelial cells, hepatocytes, breast cancer cells and osteoblasts. It would be apparent to one skilled in the art to culture the cells in the manner appropriate for optimal cell growth.

The bottom of the tissue culture dish may be coated with extracelular matrix proteins, such as collagen and laminin, to ensure attachment of cultured cells to the substrate.

In an additional embodiment of the invention, the system comprises the partially purified cytoskeleton deficient in force-dependent proteins, and exogenous proteins may include proteins involved in in force-initiated signal transduction. The exogenous proteins may comprise an extract. The extract may be a purified or crude protein extract. In a preferred embodiment of the invention, the extract is derived from a cell lysate. The extract may be derived from a cell type that is the same as the cell type from which the partially purified cytoskeleton is derived. The cells may include primary cells or established cell lines. These cells may also include, but are not limited to, L-929 cells, HEK 293 cells, tumor cells, muscle cells, hair cells, neurons, cardiac smooth muscle cells, endothelial cells, hepatocytes, breast cancer cells, osteoblasts, osteocytes, chondrocytes, and keratinocytes.

In accordance with the invention, the proteins of the extract may be labeled to enable detection of proteins bound to the partially purified cytoskeleton network. Proteins in the extract may be radiolabeled or biotinylated. In a preferred embodiment of the invention, the proteins are biotinylated. To detect the bound proteins, the detergent-insoluble cytoskeleton network is extracted and run on two dimensional (2-D) gels and immunoblotted with a Streptavidin antibody. Proteins detected on the gel may be eluted from the gel and sequenced by conventional techniques to determine the identity of the protein. Alternatively, monoclonal antibodies may be used to identify the protein within the gel. Other techniques known in the art, such as fluorescent molecules, may be employed to label and detect the bound proteins.

The present invention provides a method of identifying cytoplasmic proteins that become associated with the partially purified cytoskeleton network upon application of a force.

In one embodiment, the method of the present invention provides for identifying proteins involved in mechanotransduction comprising providing a cytoskeleton network deficient in force-dependent proteins and contacting the partially purified cytoskeleton network deficient in force-dependent proteins with exogenous proteins under conditions that allow for the exogenous proteins to bind to the partially purified cytoskeleton network, and identifying the bound proteins. The cytoskeleton network deficient in force-dependent proteins may be obtained by growing cells in culture on an elastomeric substrate being deformed in shape from induced stress. The cells are treated with a permeabilizing component to obtain a partially purified cytoskeleton network deficient in force-dependent proteins. The substrate is then deformed by stretching to apply a force to the cytoskeleton network.

The method of the present invention is useful for the screening for agents that inhibit the localization of proteins to the cytoskeleton upon force-initiated signal transduction. Screening for agents will vary depending upon the desired effect. Since mechanical force is instrumental in cell growth, differentiation, secretion, motility, or mitosis, the method may be used to screen for agents involved in these pathways. In such an embodiment, the method comprises adding a candidate agent before or during the contacting with exogenous proteins, wherein the agent may enhance or inhibit binding of one or more of the exogenous proteins. The agent may be capable of inhibiting or enhancing mechanotransduction and may therefore be useful in treating disease. The agent may also be identified by its ability to enhance or inhibit a specific protein identified by the present invention from binding to a cytoskeleton.

Cardiac smooth muscle cells and capillary endothelial cells may be used in this embodiment to identify agents that inhibit or enhance cell contractibility and produce a desired effect against hypertension.

Tumor cells may be used to screen for agents that inhibit cell motility to prevent tumor cell metastasis and invasion. Osteoblasts may be used to screen for agents that inhibit loss of bone mass.

Although the present invention has been described with reference to certain preferred embodiments, various modifications, alterations, and substitutions will be apparent to those skilled in the art without departing from the spirit and scope of the invention, as defined by the appended claims.

EXAMPLES

Materials and Methods

Cells, Transfection and Plasmids

Mouse fibroblast L-929 cells and HEK 293 cells were cultured in Dulbecco Modified Eagle Media (Invitrogen, Carlsbad, Calif.) supplemented with 10% FBS at 37° C., 5% $CO_2$ and 100% humidity. Transfection was performed with FuGene 6 (Roche) according to the manufacturer's protocol. GFP paxillin expression vector, GFP vinculin expression vector and parent GFP expression vector (pRK-GFP) were provided by K. Yamada (NIH). To isolate cell lines stably expressing transfected GFP paxillin or GFP (without paxillin), pcDNA3 that carried a neomycin-resistant gene (Invitrogen, Carlsbad, Calif.) was cotransfected and clones were selected using G418 (Invitrogen, Carlsbad, Calif.).

Preparation of Triton X-100-Insoluble Cytoskeletons

L-929 cultures were plated on collagen-coated (type 1, Sigma-Aldrich, St. Louis, Mo.) silicone, using either the Stage-Flexer system (Flexcell International, Hillsborough, N.C.) or the stretchable silicone dishes as described in Sawada et al. (J. Cell Science 2001. 114:1221–1227). Cells were washed once with isotonic ISO buffer (20 mM Hepes, pH 7.5, 150 mM NaCl, 0.5 mM EDTA, 1 mM DTT, 4 mM $MgCl_2$, 1 mM PMSF, 15 μg/ml aprotinin), treated with 0.25% Triton X-100/ISO(+) buffer (ISO buffer supplemented with 0.5 mM ATP, 2% BSA) for 2 min. and washed three times with ISO (+) buffer.

Observation of Stretch-dependent (GFP) Paxillin Assembly in Intact Cells

Subconfluent L-929 cells transiently transfected with GFP paxillin in the collagen-coated (type I) silicone membrane (Flexcell International, Hillsborough, N.C.) were stretched biaxially (10% in each dimension) for 2 min., and the GFP fluorescence was observed by fluorescence microscopy. Five min after stretch, the silicone substrate was relaxed to its original size, and the fluorescence was recorded. For endogenous paxillin measurement, L-929 cells cultured in silicone membranes were stretched likewise for 2 min, and fixed with 3.7% formaldehyde/PBS. After fixation, the cells on the silicone substrate were permeabilized with 0.1% Triton X-100/PBS, subjected to immunostaining using anti-paxillin antibody (Transduction Labs, Mississauga, ON, CANADA) or anti-vinculin antibody (Upstate Biotechnology, Waltham, Mass.) and compared with cells that had been fixed before stretch.

Preparation of Lysates from 293-GFP-pax Cells or L-929 Cells

HEK 293 cells stably transfected with GFP paxillin expression vector (293-GFP-pax cells) or L-929 cells were scraped off tissue culture plastic, washed twice with ISO buffer, resuspended 1:1.5 (packed cells:buffer) in hypotonic (HYPO) buffer (20 mM Hepes, pH 7.5 0.5 mM EDTA, 1 mM DTT, 4 mM $MgCl_2$, 1 mM PMSF, 15 μg/ml aprotinin), homogenized, and cleared of cell debris and nuclei of centrifugation ($2\times10^5$ g, 30 min.). The supernatant was filtrated using PD-10 column (Amersham Pharmacia Biotech, Piscataway, N.J.) preequilibrated with ISO buffer. Approximately 7 ml of lysate containing approximately 5 mg/ml of cytoplasmic proteins can be obtained from $4\times10^2$ of cells grown to confluence.

Biotinylation of Lysates from L-929 cells

After passage over the PD-10 column preequilibrated with ISO buffer, lysates from L-929 cells were incubated with NHS-biotin or NHS-PC-LC-biotin (100 μg/ml) (Pierce Chemical Co., Rockford, Ill.) for 2 hr at 4° C. and then passed over a second PD-10 column preequilibrated with ISO buffer to remove unbound biotin.

Stretch-protocol of Triton-X-100-insoluble Cytoskeleton

L-929 cells were cultured on the silicone substrate and Triton X-100 treated for 2 minutes, as indicated above. Thereafter, the Triton-X-100-insoluble cytoskeleton was washed 3 times with ISO(+) buffer to remove Triton X-100 and remaining Triton-soluble cellular components. After the third wash, the Triton X-100-insoluble cytoskeleton in ISO (+) buffer was left unstretched, stretched for 15 sec, or relaxed (pre-stretched and released from the stretch). The buffer was replaced with the lysate from L929 cells or 293 cells stably transfected with GFP paxillin and incubated for 2 minutes. The lysate was washed 4 times with ISO(+) buffer.

2-D Gel Electrophoresis

The bound complex of proteins were solubilized with 1 ml of rehydration buffer (8M urea, 2% CHAPS, 20 mM DTT, 0.5% IPG buffer (Amersham Pharmacia Biotech, Piscataway, N.J.) for isoelectric focusing. Immobiline dry strip (pH 4–7) (Amersham Pharmacia Biotech, Piscataway, N.J.) was rehydrated with 350 µl of each sample and subjected to isoelectric focusing followed by SDS-PAGE. Biotinylated cytoplasmic proteins in 2-D gels were visualized with affinity blotting using HRP-conjugated Streptavidin.

Fluorescent Microscopy

Triton-X-100-insoluble cytoskeletons on a collagen-coated silicone membrane (StageFlexer®, Flexcell International, Hillsborough, N.C.) were incubated with rhodamine-phalloidin (Molecular Probes, Eugene, Oreg.) for 2 min. and washed three times with ISO(+) buffer. Images were obtained with an Olympus BX50 microscope with a 60×, 0.9 NA water immersion objective. Images were obtained before stretch, and 5 minutes after stretch.

GFP fluorescence of L-929 cells transfected with GFP-paxillin were also observed with an Olympus BX50 microscope with a 60×, 0.9 NA water immersion objective.

For immunostaining, cells were fixed with 3.7% formaldehyde/PBS, perneabilized with 0.1% Triton X-100/PBS before incubation with antibodies to paxillin and vinculin.

Western Blotting

L-929 cytoplasmic proteins were tagged with a photocleavable biotin (NHS-PC-LC-biotin) and added to Triton X-100-insoluble cytoskeletons of L-929 cells on a stretchable silicone dish. Cytoskeletons were stretched or unstretched. Bound cytoplasmic proteins were washed and eluted with HYPO buffer (20 mM Hepes, pH 7.5 0.5 mM EDTA, 1 mM DTT, 4 mM MgCl2, 1 mM PMSF, 15 µg/ml aprotinin), precipitated with avidin beads (immobilized neutravidin, Pierce Chemical, Co., Rockford, Ill.) after several fold dilution with HYPO buffer and released from the bead complex by irradiation with 302 nm UV light for 10 minutes. After photocleavage, proteins were eluted with 120 µl HYPO buffer, and 40 µl of the sample was subjected to 10% SDS-PAGE followed by immunoblotting with antibodies to paxillin, FAK, p130Cas, PKB/Akt (Transduction Laboratories, Mississauga, ON, CANADA), vinculin (Upstate Biotechnologies, Waltham, Mass.) and actin (Santa Cruz Biotechnology, Santa Cruz, Calif.).

RESULTS

To test whether or not the stretching of cytoskeletons could lead to cytoplasmic binding, a protocol was designed to screen for cytoplasmic proteins that bind in a stretch-dependent manner to Triton X-100-insoluble cytoskeletons, as shown in FIG. 1. Treatment of cells with 0.25% Triton X-100 releases most cytoplasmic and membrane proteins including the majority of focal contact proteins paxillin, focal adhesion kinase (FAK), p130Cas, and vinculin, with the cytoskeleton attached to the collagen-coated substrate. The cytoskeleton remains attached to the substrate during biaxial stretch of 10% as measured by changes in the dimension of phalloidin-labeled cytoskeletons.

To control the general effects of mechanical disturbance and the traction forces normally generated under routine culture conditions (Galbraith and Sheetz, 1997, J. Cell Biol. 147:1313–1324; Horwitz and Parsons, 2001, J. Cell. Sci. 114:1221–1227), a set of cells were incubated overnight in a prestretched substratum (Sawada et al. 2001, J. Cell Sci. 114:1221–1227), treated with Triton X-100, and the remaining cytoskeletons were relaxed.

Cytoplasmic proteins from L-929 cells were biotinylated to differentiate them from Triton X-100-insoluble cytoskeletal proteins. Biotinylated cytoplasmic proteins were incubated with stretched or relaxed cytoskeletal structures. The bound complexes were washed and solubilized for two-dimensional (2-D) gel electrophoresis and blot analysis using HRP-conjugated Streptavidin (Amersham Pharmacia Biotech, Piscataway, N.J.) in more than 10 separate experiments.

Figure 2:
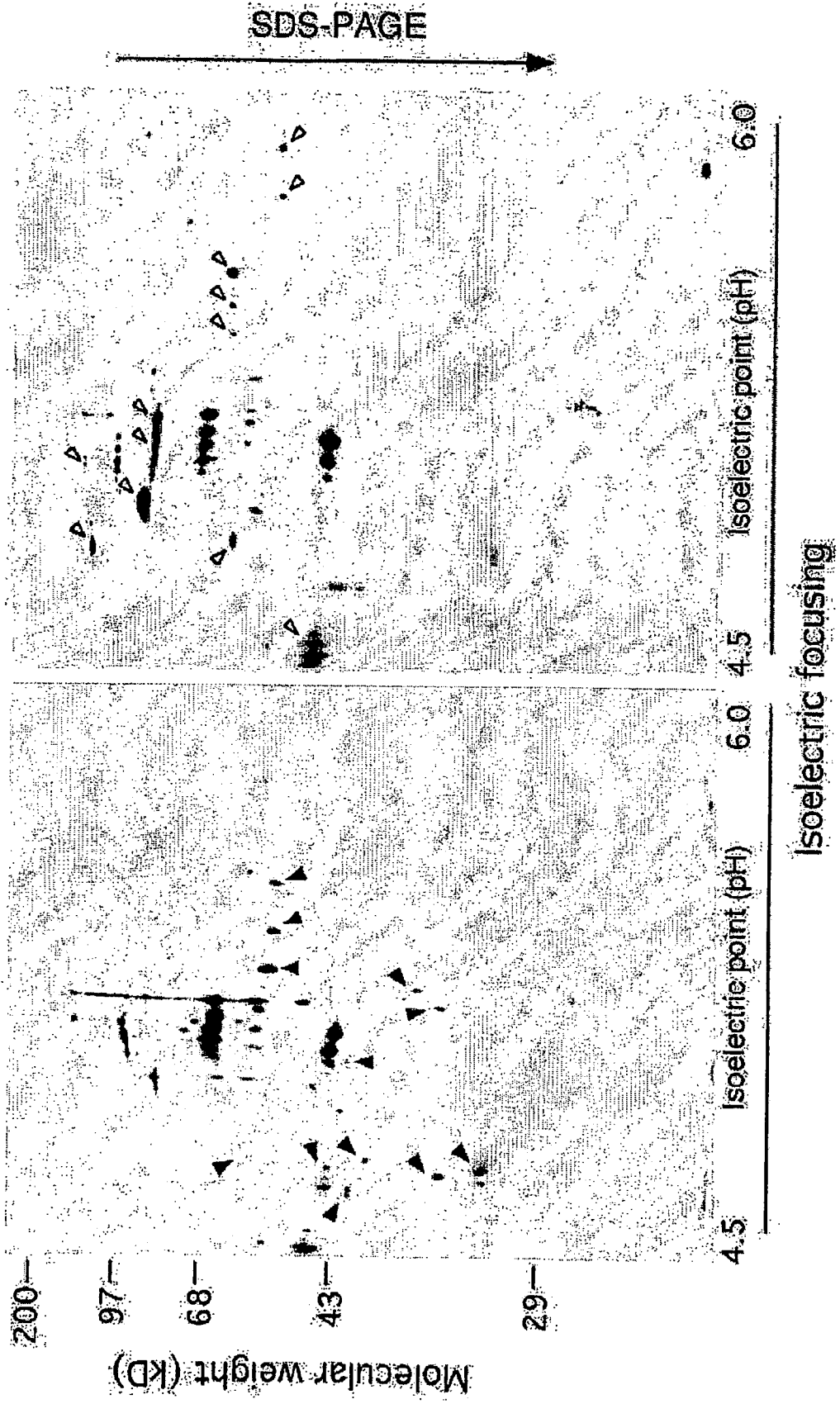
FIG. 2 shows 2-D gels of proteins that bound to stretched (A) or relaxed (B) cytoskeletons.

More than 10 major and several minor stretch-specific protein spots were reproducible found, as shown in the 2-D gel of FIG. 2A. Approximately 10 major and several minor spots were specific to the relaxed Triton X-100-insoluble cytoskeleton, as shown in the 2-D gel of FIG. 2B.

In a separate experiment, no difference in the binding of biotinylated cytoplasmic proteins to cytoskeletons after incubation of the cells for 16 hr on an unstretched or prestretched (but relaxed) substrate was observed. This result indicated that prestretching the substrate had no effect. Thus, stretching or relaxing of a substrate causes the reproducible binding of biotinylated cytoplasmic proteins to Triton X-100-insoluble cytoskeletons.

Numerous controls were performed to test for binding of biotinylated proteins to the substratum or collagen, but the pattern of stretch-specific spots was not repeated. Further, the adhesion of cells to the collagen substrate was necessary, since stretching of substrata when cells were not spread, i.e. cells were cultured on uncoated silicone substrate, did not cause stretch-dependent binding. If the cells have reached confluence, then stretching of a confluent monolayer of Triton X-100-insoluble cytoskeleton did not result in stretch-dependent binding. These results indicate that cell cytoskeleton-matrix linkages must be stretched to cause stretch-dependent binding.

Figure 3:
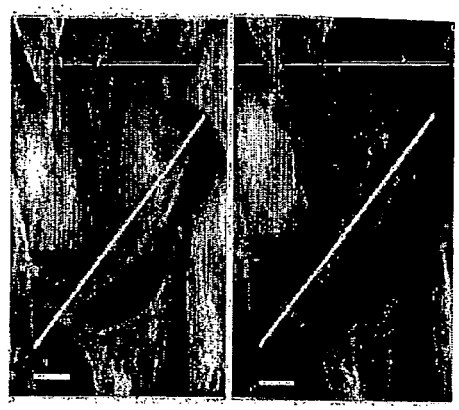
FIG. 3A is an immunofluorescent micrograph of Triton X-100-insoluble cytoskeletons before and after stretch.
FIG. 3B shows Western blots of focal contact proteins that bound to stretched and unstretched cytoskeletons.
Figure 3:
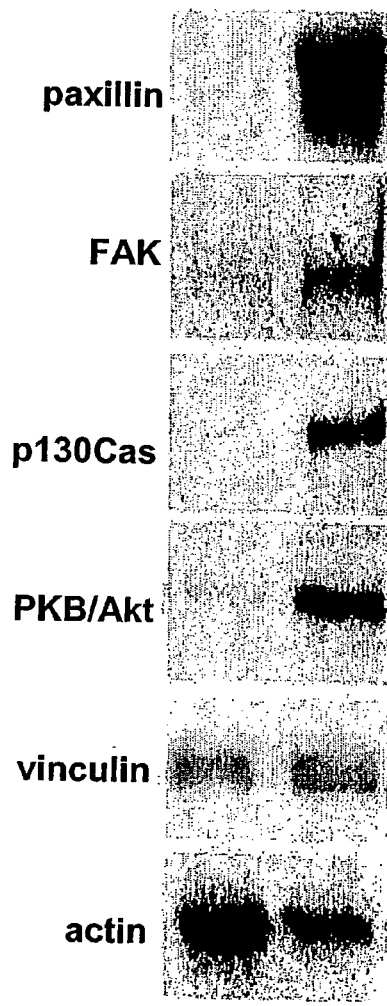

Since focal contacts grow in response to stretch, focal contact proteins association with the cytoskeletons in response to a 10% stretch of the cytoskeletons was assayed. Immunofluorescent micrographs of Triton X-100 cytoskeletons before and after stretching are shown in FIG. 3A. To enable the purification of bound cytoplasmic proteins from Triton X-100-insoluble cytoskeletons, the cytoplasmic proteins were labeled with a photocleavable form of biotin (Olejnik et al., 1995, Proc. Natl. Acad. Sci. 92:7590–7594). Biotinylated proteins eluted from the cytoskeletons by high salt were bound to avidin beads, released by UV radiation, and subjected to SDS-PAGE followed by immunoblot analysis. Using monospecific antibodies to paxillin, FAK, p130Cas, and vinculin, increased binding of the paxillin, FAK, and p130Cas to stretched cytoskeletons was observed. However, vinculin binding did not change with cells on the collagen matrix, as shown in FIG. 3B. In addition, stretch-dependent binding of PKB-Akt was observed (King et al., 1997, Mol Cell Biol. 17:1106–1118). Interestingly, actin binding decreased by approximately 50% (n=5) in the samples from the stretched cytoskeletons, as shown in the Western blots of various focal contact proteins that bound to stretched and unstretched cytskelons in FIG. 3B. Since the binding of vinculin and actin remained constant or decreased, respectively, it is clear that stretch does not cause all focal contact proteins to bind to the cytoskeletons.

Since paxillin, FAK, and p130Cas are known to form complexes (Harte et al., 1996, J. Biol. Chem. 271:13649–13655; Bang et al. 2000 Biochem. Biophys. Res. Comm. 278:522–529; Yano et al., 2002, Proc. Natl. Acad. Sci. 97:9076–9081), coimmunoprecipitation was performed using monospecific antibodies to paxillin, FAK, and p130Cas. Although coimmunoprecipitation of FAK and p130Cas was observed, paxillin was not precipitated with an antibody to FAK or p130Cas. Furthermore, neither FAK nor p130Cas was precipitated with an antibody to paxillin. Thus, it is likely that three of the identified proteins, paxillin, Akt/PKB and FAK-p130Cas complex, bind independently to the cytoskeletons.

Figure 4:
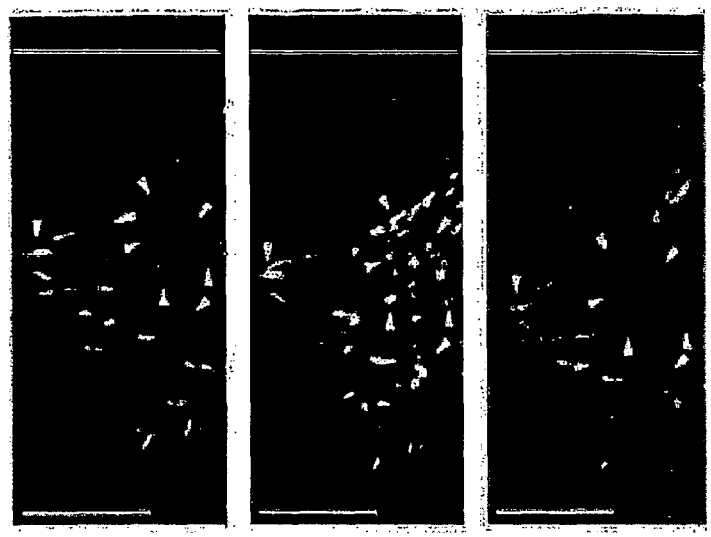
FIG. 4A shows fluorescent micrographs of GFP-paxillin localization of intact L-929 cells before stretch, after stretch and relaxed post-stretch.
FIG. 4b shows fluorescent micrographs of endogenous paxillin, and vinculin localization of intact L-929 cells before and after stretch.
Figure 4:
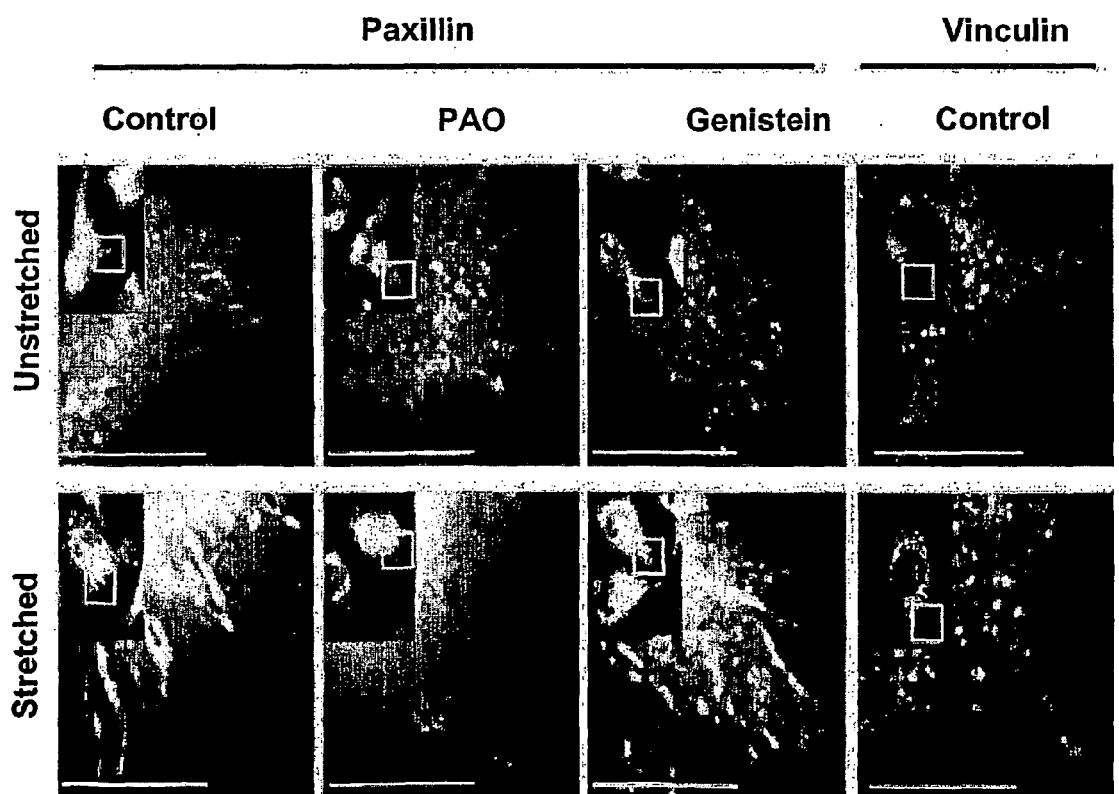

After L-929 cells were transfected with GFP-paxillin in a collagen-coated silicone substrate, there were relatively few focal contacts labeled with GFP paxillin, as shown in the fluorescent micrograph of GFP paxillin localization in intact L-929 cells at the left of FIG. 4A. However, when the cells were stretched biaxially (10% in each direction), the GFP fluorescence at focal contacts increased dramatically, particularly at the periphery of cells, as shown in the fluorescent micrograph of GFP paxillin localization in intact L-929 cells in the middle of FIG. 4A. Relaxation of the stretched cells resulted in the rapid, i.e. less than 2 min., loss of peripheral GFP paxillin assembly at focal contacts, as shown in the fluorescent micrograph of GFP paxillin localization in intact L-929 cells at the right of FIG. 4A. Immunocytochemical analysis showed that the endogenous paxillin behaved similarly, as shown in the fluorescent micrograph of endogenous paxillin localization in intact L-929 cells in FIG. 4B. Referring to FIG. 4B, it may be seen that the stretch-dependent paxillin accumulation was inhibited by addition of a tyrosine phosphate inhibitor, phenylarsine oxide (PAO, 2 $\mu$M), whereas it was not inhibited by a tyrosine kinase inhibitor, genistein (100 $\mu$M) (Akiyama et al., 1987, J. Biol Chem. 262:5592–5595), implying that tyrosine dephosphorylation of some molecule was required for assembly as seen in other systems (Choquet et al., 1997, Cell 88:39–48).

In contrast to Balaban et al. (2001, Nat. Cell Biol. 3:466–472) and Riveline et al. (2001, J. Cell Biol. 153: 1175–1186), who have published that GFP vinculin assemble at the focal contact sites in a force-dependent manner, there was no stretch-dependent accumulation of endogenous vinculin, as shown by the fluorescent micrograph at the right of FIG. 4B, or GFP vinculin at the focal adhesions.

To test whether or not paxillin would bind to the stretched cytoskeletons in a location and manner similar to intact cells, cytoplasmic proteins from HEK 293 cells stably transfected with GFP-paxillin (293-GFP-paxillin) were added to the stretched cytoskeletons. The GFP moiety differentiates the added paxillin from the small amount of endogenous paxillin that remained in Triton X-100-insoluble cytoskeletons of L-929. After biaxial stretch, it was found that GFP paxillin bound with a punctate distribution concentrated at the lower surface of cells, as shown by the fluorescent micrograph at the top of FIG. 5A. This is similar to the distribution of endogenous paxillin binding in stretched intact cells, as shown by the fluorescent micrograph at the lower left of FIG. 4B. Using cytoplasmic proteins from HEK 293 cells stably transfected with GFP only, it was found that GFP alone did not bind to Triton X-100-insoluble cytoskeletons whether stretched or not. Therefore, the in vitro GFP paxillin binding to the Triton X-100-insoluble cytoskeletons is analogous to in vivo stretch-dependent paxillin binding.

Figure 5A:
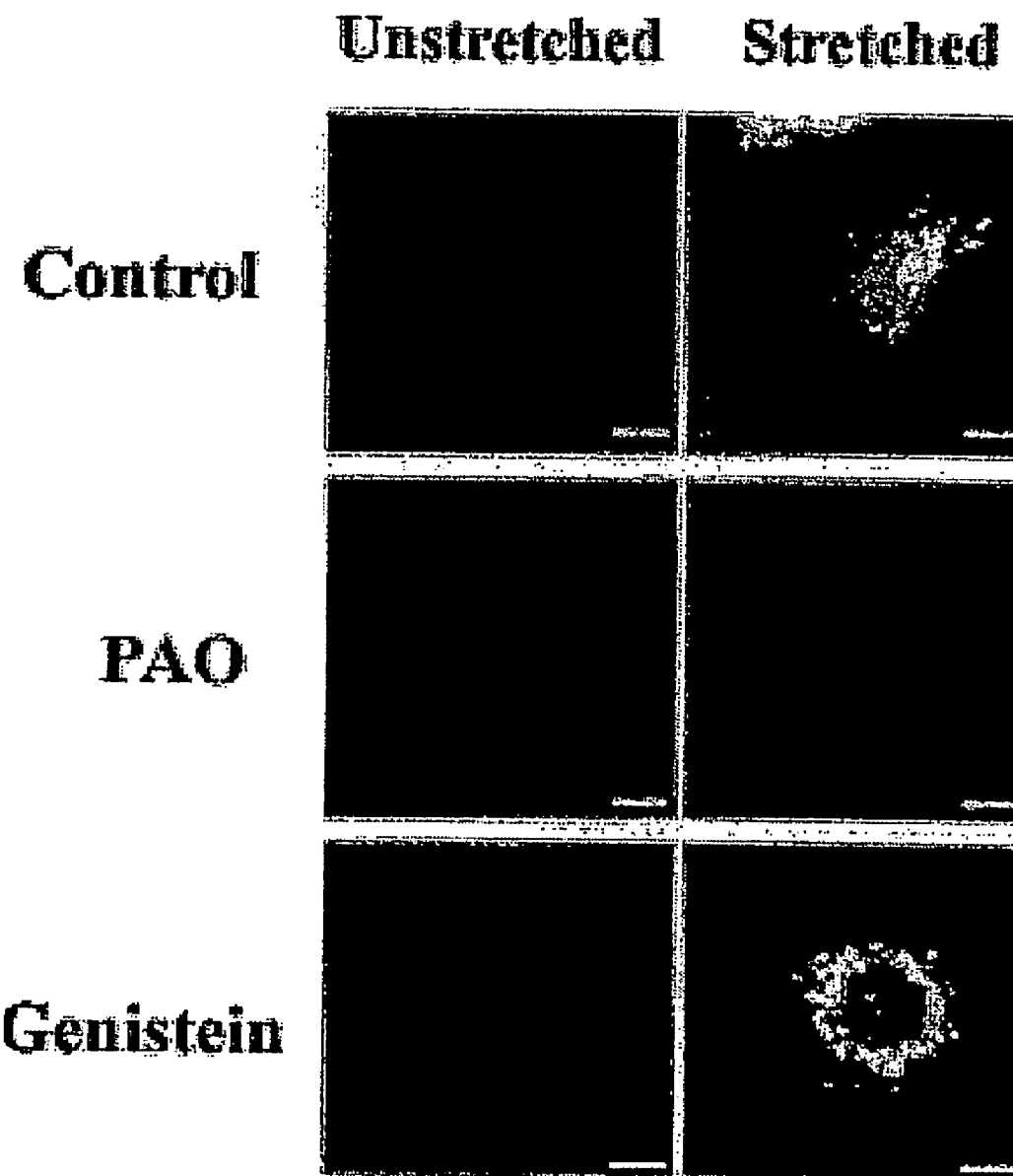
FIG. 5A shows GFP paxillin binding in PAO and genistein-treated Triton X-100 insoluble cytoskeletons that are stretched and unstretched.

With subconfluent L-929 cell monolayers ($4\times10^5$ cells/dish), stretch-dependent GFP paxillin binding was observed, which was consistent with the microscopic findings, as shown in FIG. 5A. Cytoskeleton number as measured by histone H1 was constant. However, with confluent L-929 monolayers ($1.2\times10^6$ cells/dish) GFP paxillin did not bind to the stretched Triton X-100-insoluble cytoskeletons, as shown in FIG. 5D. Referring to FIG. 5D, an increased amount of histone H1 is noted in the right four lanes.

Figure 5B:
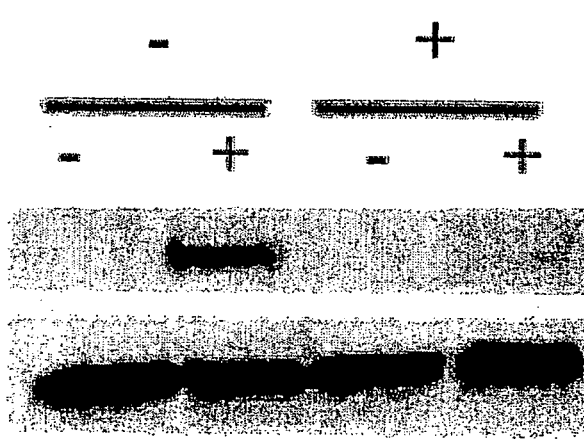
FIG. 5B is a Western blot showing that GFP-paxillin binds to stretched Triton X-100 insoluble cytoskeletons that have not been treated with PAO.
Figure 5C:
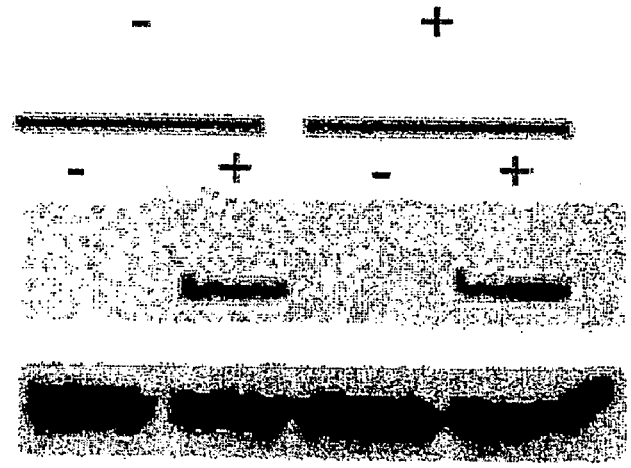
FIG. 5C is a Western blot showing that GFP-paxillin binds to stretched Triton X-100 insoluble cytoskeletons in the presence and absence of PAO-Sodium orthovanadate treatment.
Figure 5D:
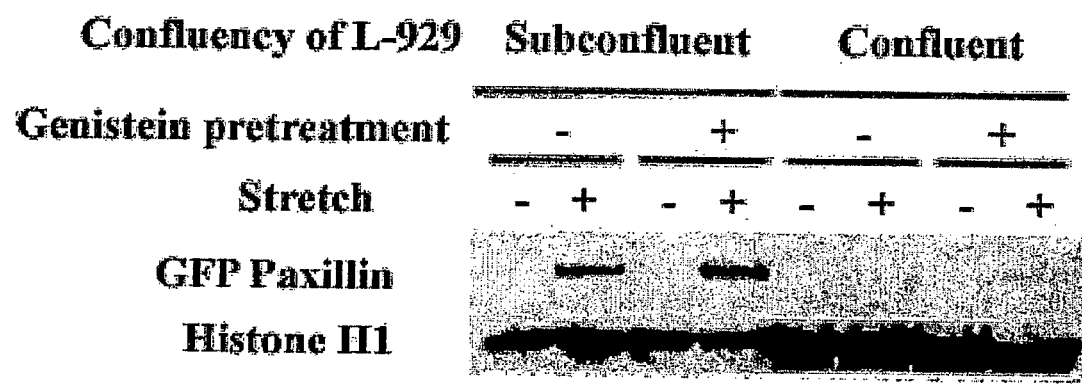
FIG. 5D is a Western blot showing that GFP-paxillin binds to stretched Triton X-100 insoluble cytoskeletons in the presence and absence of genistein treatment.

Treatment of the cells with PAO prior to Triton extraction decreased the amount of GFP paxillin bound to the stretched cytoskeletons, as shown in the fluorescent micrograph at the right side of the middle row of FIG. 5A and the Western blot of FIG. 5B. Whereas, genistein treatment caused an increase in the amount of GFP paxillin bound to the stretched subconfluent cytoskeleton, as shown in the fluorescent micrograph at the right of the lower row of FIG. 5A and in the Western blot of FIG. 5D. Addition of PAO to lysates did not affect the stretch-dependent GFP paxillin binding even when another tyrosine phosphorylation inhibitor, sodium orthovandate $NA_3VO_4$, 1 mM), was added and DTT was excluded to ensure the inhibition of tyrosine phosphatase activity by PAO (Stover et al.), as shown in FIG. 5C. Furthermore, the lysates obtained from 293 GFP-pax cells pretreated with PAO showed equivalent stretch-dependent GFP paxillin binding to the control samples. Because PAO inhibition was only observed when L-929 cells were pretreated and GFP paxillin binding to the cytoskeleton was ATP independent, the binding is likely to be independent of either protein kinase or phosphatase activity.

It was found that cytoskeletons prepared from cells treated with PAO could be stretched by at least two-fold more than that of the control untreated samples, indicating that they had decreased integrity. Early reinforcement of extracellular matrix linkages with the cytoskeleton is inhibited by PAO (Choquet et al. 1997 Cell 276:1425–1428). An expected result of PAO treatment of dynamic linkages would be a decrease in the strength of cytoplasmic-matrix linkages, since they could not reform. In contrast, PAO treatment of cytoskeletons prepared from cells not treated with PAO, did not cause any change in the Triton cytoskeleton integrity perhaps because of the lack of dynamics. Thus, cytoskeleton integrity appears to be important for stretch-dependent binding.

A decrease in cytoskeletal integrity would result in lower forces in the Triton cytoskeleton after stretch. Hence, force on the Triton cytoskeleton is critical for binding. Further, force on cytoskeleton-integrin-matrix linkages appears to be critical. When cells become confluent, the area of adherence to the matrix substrate is decreased and cell-cell contacts are increased. Thus, the loss of stretch-dependent paxillin-binding, in confluent cells implicates the matrix-cytoskeleton linkage. Without wishing to be bound by theory or mechanism, it is believed that force on the collagen-integrin-cytoskeleton linkage causes protein or domain unfolding, which results in binding.

From the analysis of the biotinylated proteins that bind to the cytoskeletons, it is clear that a distinct subset of proteins binds to the stretched cytoskeleton that is different from the proteins that bind to the relaxed cytoskeleton. The limited number of proteins that bind in specific manner is consistent with a selective binding process. Because an extracted cytoskeleton and cytoplasm that had been manipulated, i.e.

diluted, biotinylated and column filtered was used, there may be additional components that bind in vivo to cytoskeletons.

What is claimed is:

1. A system for the identification of proteins involved in mechanotransduction comprising:
    a cytoskeleton network deficient in force-dependent proteins,
    exogenous proteins in contact with the cytoskeleton network,
    means for applying a force to the cytoskeleton network; and
    means for identifying any of the exogenous proteins that bind to the cytoskeleton network when a force is applied to the cytoskeleton network,
    wherein exogenous proteins identified as being bound to the cytoskeleton network with the force applied thereto are identified as proteins involved in mechanotransduction.

2. The system of claim 1, wherein the cytoskeleton network is attached to a deformable substrate having a surface area, and the force is applied to the cytoskeleton network by deforming the substrate so as to apply the force to the cytoskeleton network.

3. The system of claim 2, wherein the deformable substrate comprises an elastomeric material.

4. The system of claim 2, wherein the cytoskeleton network is deformed by the force applied to thereto.

5. The system of claim 1, wherein the cytoskeleton network is prepared from cultured cells.

6. The system of claim 5, wherein the cells are treated with a component to obtain the cytoskeleton network.

7. The system of claim 6, wherein the component is selected from the group consisting of alcohols, enzymes and detergents.

8. The system of claim 7, wherein the detergent is a non-ionic detergent.

9. The system of claim 8, wherein the detergent is saponin.

10. The system of claim 5, wherein the cells are selected from the group consisting of primary cells and established cell lines.

11. The system of claim 10, wherein the established cell line is selected from the group consisting of L-929 cells, HEK 293 cells, tumor cells, muscle cells, hepatocytes, cardiac smooth muscle cells, hair cells, neuronal cells, osteoblasts, osteocytes, chondrocytes, keratinocytes and endothelial cells.

12. The system of claim 11, wherein the cell line is L-929 cells.

13. The system of claim 2, wherein the deformable substrate is the bottom of a tissue culture dish.

14. The system of claim 2, wherein the deformable substrate is deformed by the application of physical force thereto.

15. The system of claim 14, further comprising a stretch frame on which the substrate is mounted, wherein the substrate is deformed by expanding the stretch frame.

16. The system of claim 2, wherein the substrate is deformed by stretching the substrate to expand the surface area thereof.

17. The system of claim 16, wherein the surface area is expanded from about 5% to about 50% of the surface area of the substrate prior to stretching.

18. The system of claim 17, wherein the surface area is expanded by about 10% of the surface area of the substrate prior to stretching.

19. The system of claim 2, wherein the substrate is deformed by contraction so as to reduce the surface area of the substrate.

20. The system of claim 19, wherein the surface area is reduced from about 5% to about 35% of the surface area of the substrate prior to contraction thereof.

21. The system of claim 20, wherein the surface area is reduced by about 10% of the original surface area of the substrate prior to contraction thereof.

22. The system of claim 1, wherein the exogenous proteins are prepared from cells.

23. The system of claim 22, wherein the cells are selected from the group consisting of L929 cells, HEK 293 cells, tumor cells, muscle cells, hepatocytes, cardiac smooth muscle cells, hair cells, neuronal cells, osteoblasts, osteocytes, chondrocytes, keratinocytes and endothelial cells.

24. The system of claim 1, wherein the exogenous proteins are radiolabeled.

25. The system of claim 1, wherein the exogenous proteins are biotinylated.

26. A method of identifying proteins involved in mechanotransduction comprising:
    providing a cytoskeleton network deficient in force-dependent proteins;
    contacting the cytoskeleton network with exogenous proteins,
    applying a force to the cytoskeleton network, and
    identifying the exogenous proteins that bind to the cytoskeleton network when the force is applied thereto, wherein the exogenous proteins that bind to the cytoskeleton network are identified as proteins involved in mechanotransduction.

27. The method of claim 26, wherein the cytoskeleton network is prepared by
    growing cells in culture on a deformable substrate having a surface area,
    treating the cells with a component to obtain a cytoskeleton network deficient in force-dependent proteins, and
    deforming the substrate to apply a force to the cytoskeleton network.

28. The method of claim 27, wherein the deformable substrate comprises an elastomeric material.

29. The method of claim 27, wherein the deformable substrate deforms when a force is applied thereto.

30. The method of claim 27, wherein the cytoskeleton network remains attached to the deformable substrate.

31. The method of claim 27, wherein the deformable substrate is a part of a tissue culture dish.

32. The method of claim 27, wherein the cells are mammalian cells.

33. The method of claim 32, wherein the cells are selected from the group consisting of primary cells and established cell lines.

34. The method of claim 33, wherein the established cell lines are selected from the group consisting of tumor cells, muscle cells, hepatocytes, cardiac smooth muscle cells, hair cells, neuronal cells, osteoblasts, osteocytes, chondrocytes, keratinocytes and endothelial cells.

35. The method of claim 27, wherein the component is selected from the group consisting of alcohols, enzymes and detergents.

36. The method of claim 27, wherein the detergent is a non-ionic detergent.

37. The method of claim 36, wherein the detergent is saponin.

38. The method of claim 27, wherein the substrate is deformed by mechanically expanding a stretch frame that is attached to the substrate.

39. The method of claim 27, further comprising stretching the substrate to expand the surface area of the substrate.

40. The method of claim 39, wherein the surface area is expanded from about 5% to about 50% of the surface area of the substrate prior to the stretching thereof.

41. The method of claim 40, wherein the surface area is expanded about 10% of the surface area of the substrate prior to the stretching thereof.

42. The method of claim 27, further comprising contracting the substrate to reduce the surface area thereof.

43. The method of claim 42, wherein the surface area of the substrate is reduced from about 5% to about 35% of the surface area of the substrate prior to the contraction thereof.

44. The method of claim 43, wherein the surface area is reduced about 10% of the surface area of the substrate prior to the contraction thereof.

45. The method of claim 26, wherein the exogenous proteins are prepared from cells.

46. The method of claim 45, wherein the cells are selected from the group consisting of L929 cells, HEK 293 cells, tumor cells, muscle cells, hepatocytes, cardiac smooth muscle cells, hair cells, neuronal cells, osteoblasts, osteocytes, chondrocytes, keratinocytes and endothelial cells.

47. The method of claim 26, further comprising radiolabeling the exogenous proteins.

48. The method of claim 26, further comprising biotinylating the exogenous proteins.

49. A method of identifying an agent that inhibits or enhances mechanotransduction comprising:
a) providing a cytoskeleton network deficient in force-dependent proteins;
b) contacting the cytoskeleton network with exogenous proteins in the absence of the agent;
c) applying a force to the cytoskeleton network;
d) measuring an extent of binding of each of the exogenous proteins to the cytoskeleton network having the force applied thereto in the absence of the agent; and
e) contacting the cytoskeleton network with the exogenous proteins in the presence of the agent;
f) measuring the extent of binding of each of the exogenous proteins to the cytoskeleton network having the force applied thereto in the presence of the agent; and
g) determining from the measurements in steps d) and f) whether the presence of the agent increases or decreases the extent to which each of the exogenous proteins bind to the cytoskeleton network so as to determine whether the agent inhibits or enhances mechanotransduction.

50. The method of claim 49, wherein the cytoskeleton network is prepared by
growing cells in culture on a deformable substrate,
treating the cells with a component to obtain a cytoskeleton network deficient in force-dependent proteins, and
deforming the substrate so as to apply a force to the cytoskeleton network.

51. The method of claim 50, wherein the substrate deforms in shape by applying a force thereto.

52. The method of claim 50, wherein the cytoskeleton network remains attached to the substrate.

53. A method for identifying an agent capable of inhibiting or enhancing mechanotransduction comprising:
a) providing a cytoskeleton network deficient in force-dependent proteins;
b) contacting the cytoskeleton network with an identified force-dependent protein in the absence of an agent;
c) applying a force to the cytoskeleton network;
d) measuring an extent of binding of the identified force-dependent protein to the cytoskeleton network having the force applied thereto in the absence of the agent;
e) contacting the cytoskeleton network with the identified force-dependent protein in the presence of the agent;
f) measuring an extent of binding the identified force-dependent protein to the cytoskeleton network having the force applied thereto in the presence of the agent; and
g) determining from the measurements in steps d) and f) whether the presence of the agent increases or decreases the extent the identified force-dependent protein binds to the cytoskeleton network having the force applied thereto so as to determine whether the agent inhibits or enhances mechanotransduction.

* * * * *